(12) United States Patent
Belafsky

(10) Patent No.: US 11,167,116 B2
(45) Date of Patent: Nov. 9, 2021

(54) UPPER ESOPHAGEAL SPHINCTER DILATOR

(71) Applicant: The Regents of the University of California, Oakland, CA (US)

(72) Inventor: Peter Belafsky, Sacramento, CA (US)

(73) Assignee: The Regents of the University of California, Oakland, CA (US)

(*) Notice: Subject to any disclaimer, the term of this patent is extended or adjusted under 35 U.S.C. 154(b) by 131 days.

(21) Appl. No.: 16/047,950

(22) Filed: Jul. 27, 2018

(65) Prior Publication Data

US 2019/0117941 A1  Apr. 25, 2019

Related U.S. Application Data

(63) Continuation of application No. 14/398,414, filed as application No. PCT/US2013/039974 on May 7, 2013, now Pat. No. 10,052,462.

(60) Provisional application No. 61/643,852, filed on May 7, 2012.

(51) Int. Cl.
*A61M 25/10* (2013.01)
*A61M 29/02* (2006.01)

(52) U.S. Cl.
CPC .... *A61M 25/1002* (2013.01); *A61M 25/1011* (2013.01); *A61M 29/02* (2013.01); *A61M 2025/105* (2013.01); *A61M 2025/1081* (2013.01); *A61M 2025/1084* (2013.01); *A61M 2210/105* (2013.01)

(58) Field of Classification Search
CPC .... A61M 2025/105; A61M 2025/1081; A61M 2025/1084; A61M 2210/105; A61M 25/1002; A61M 25/1011; A61M 29/02; A61M 25/10; A61M 2025/1015; A61M 25/1025

See application file for complete search history.

(56) References Cited

U.S. PATENT DOCUMENTS

| | | | |
|---|---|---|---|
| 4,447,227 A * | 5/1984 | Kotsanis | A61B 17/0218 604/908 |
| 4,787,388 A * | 11/1988 | Hofmann | A61M 25/1002 604/913 |
| 4,791,923 A | 12/1988 | Shapiro | |
| 4,878,495 A * | 11/1989 | Grayzel | A61M 25/1011 606/193 |

(Continued)

FOREIGN PATENT DOCUMENTS

| EP | 1683541 | 9/2006 |
|---|---|---|
| WO | 9841167 | 9/1998 |

(Continued)

OTHER PUBLICATIONS

International Search Report and Written Opinion dated Jul. 26, 2013, from PCT Application No. PCT/US2013/039974 (10 pages).

(Continued)

*Primary Examiner* — Quynh-Nhu H. Vu
(74) *Attorney, Agent, or Firm* — Kilpatrick Townsend and Stockton LLP

(57) ABSTRACT

An apparatus for dilating an upper esophageal sphincter. The apparatus includes an elongated expandable member having a cross-section shaped to support a natural shape of an upper esophageal sphincter. A catheter extends from the elongated inflatable member.

6 Claims, 2 Drawing Sheets

(56) References Cited

U.S. PATENT DOCUMENTS

| | | | |
|---|---|---|---|
| 5,116,305 A | 5/1992 | Milder et al. | |
| 5,383,856 A * | 1/1995 | Bersin | A61M 25/1002 |
| | | | 604/101.01 |
| 5,501,667 A * | 3/1996 | Verduin, Jr. | A61M 25/1011 |
| | | | 604/101.01 |
| 5,505,702 A * | 4/1996 | Arney | A61M 25/104 |
| | | | 604/101.01 |
| 5,645,529 A | 7/1997 | Fagan et al. | |
| 5,718,685 A * | 2/1998 | Roewer | A61M 25/02 |
| | | | 604/100.01 |
| 6,117,064 A * | 9/2000 | Apple | A61N 5/1002 |
| | | | 600/1 |
| 6,190,356 B1 * | 2/2001 | Bersin | A61M 25/1002 |
| | | | 604/101.01 |
| 6,773,452 B2 | 8/2004 | Shaker | |
| 6,837,868 B1 | 1/2005 | Fajnsztajn et al. | |
| 6,913,600 B2 | 7/2005 | Valley et al. | |
| 7,578,831 B2 | 8/2009 | Von Oepen et al. | |
| 7,654,997 B2 | 2/2010 | Chang et al. | |
| 7,762,985 B2 | 7/2010 | Kabrick et al. | |
| 8,088,102 B2 * | 1/2012 | Adams | A61F 2/958 |
| | | | 604/96.01 |
| 8,137,309 B2 | 3/2012 | Nishtala et al. | |
| 8,523,762 B2 | 9/2013 | Miyamoto et al. | |
| 8,663,319 B2 * | 3/2014 | Ho | A61B 17/12036 |
| | | | 623/2.11 |
| 9,060,802 B2 * | 6/2015 | Kugler | A61B 17/3207 |
| 9,186,488 B2 | 11/2015 | Tilson et al. | |
| 9,192,492 B2 | 11/2015 | Seguin et al. | |
| 2001/0016725 A1 | 8/2001 | Valley et al. | |
| 2004/0260239 A1 | 12/2004 | Kusleika | |
| 2006/0229631 A1 * | 10/2006 | Reiley | A61F 2/28 |
| | | | 606/93 |
| 2007/0299392 A1 * | 12/2007 | Beyar | A61F 2/958 |
| | | | 604/96.01 |
| 2007/0299433 A1 | 12/2007 | Williams et al. | |
| 2008/0140002 A1 * | 6/2008 | Poor | A61M 25/10 |
| | | | 604/103.02 |
| 2008/0167675 A1 | 7/2008 | Hogosta et al. | |
| 2009/0030370 A1 * | 1/2009 | Nishtala | A61M 25/04 |
| | | | 604/103.01 |
| 2009/0081299 A1 | 3/2009 | Hossainy et al. | |
| 2009/0088685 A1 | 4/2009 | Kugler et al. | |
| 2009/0240199 A1 | 9/2009 | Rahimsobhani | |
| 2010/0010470 A1 | 1/2010 | Bates | |
| 2010/0168665 A1 * | 7/2010 | Skerven | A61M 25/0155 |
| | | | 604/95.03 |
| 2011/0060275 A1 | 3/2011 | Christiansen | |
| 2012/0128863 A1 | 5/2012 | Nguyen et al. | |
| 2015/0088064 A1 | 3/2015 | Belafsky | |

FOREIGN PATENT DOCUMENTS

| | | |
|---|---|---|
| WO | 2006083217 | 8/2006 |
| WO | 2007104056 | 9/2007 |
| WO | 2007104056 | 11/2007 |
| WO | 2010078112 | 7/2010 |

OTHER PUBLICATIONS

Extended European Search Report for EP 13787311.3, dated March 3, 2016 (8 pages).

* cited by examiner

Casting of the Upper Esophageal Sphineter in Sheep

UPPER ESOPHAGEAL SPHINCTER DILATOR

CROSS-REFERENCES TO RELATED APPLICATIONS

This application is a Continuation of U.S. application Ser. No. 14/398,414, filed Oct. 3, 2014, which is a 371 U.S. National Phase of International Application No. PCT/US2013/039974, filed May 7, 2013, which claims the benefit of U.S. Provisional Patent Application No. 61/643,852, filed on May 7, 2012, the disclosures of which are incorporated in their entirety by reference herein.

BACKGROUND OF THE INVENTION

Patients often undergo radiation therapy to treat portions of the neck near the upper esophageal sphincter (UES). One side effect of such treatment is scarring and stiffening of nearby tissue, which is caused by radiation induced fibrosis. Other causes of UES dysfunction include acid reflux disease, cricopharyngeus muscle dysfunction, and upper esophageal web. To treat this affliction, an esophageal dilator can be dilated within the UES for a period of time to help remodel the scar tissue.

Current esophageal dilators are cylindrical and have been developed to dilate the esophageal body that has a round circumference. Recent animal research casting the upper esophageal sphincter (UES) in sheep suggests that the diameter of the upper esophageal sphincter is not round and that currently available dilators are inappropriate for UES dilation.

Accordingly, it would be desirable to have a device that better approximates the biomechanical dimensions of the sphincter.

BRIEF SUMMARY OF THE INVENTION

Embodiments of the invention include a balloon dilator specifically designed for the upper esophageal sphincter that more accurately approximates the biomechanical dimensions of the sphincter. Recent research in our animal lab suggests that the shape of the sphincter is similar to the shape of a kidney and dissimilar to current cylindrical dilators with a round circumference.

The dilator may be shaped like a kidney or it may include two cylindrical dilators in direct apposition to each other. Two cylindrical dilators in apposition more appropriately approximate the dimensions of the UES than one dilator. Other embodiments of the invention include specific means of fabricating a balloon dilator in the kidney shape of the UES. The two cylindrical dilators or the one kidney shaped dilator may be incorporated into one delivery catheter or two separate catheters. A single catheter delivery system may have two separate ports to inflate each side of the balloon separately or one port to dilate the entire dilator at once. If two separate catheters are used there may be a feature that allows each side of the balloon catheter to be inflated separately or at the same time.

Embodiments of the invention include a device having an elongated expandable member. The elongated expandable member can have a cross-section shaped to support a natural shape of an upper esophageal sphincter. A catheter may extend from the elongated inflatable member.

In some embodiments, the elongated expandable member includes a first elongated balloon adjacently coupled to a second elongated balloon.

In some embodiments, the device includes an outer sheath wrapped around the first and second elongated balloons.

In some embodiments, the device includes a central guide member located between the first and second elongated balloons.

In some embodiments, the balloons are configured to be differentially inflated.

In some embodiments, the elongated expandable member comprises an elongated expandable balloon having a kidney shaped cross-section.

In some embodiments, the balloon is constructed from a non-compliant or semi-compliant material.

In some embodiments, the elongated expandable member is configured to elute a therapeutic substance.

Embodiments of the invention are also related to a method for dilating an upper esophageal sphincter. In the method, an elongated expandable member is inserted into an interior passageway of an upper esophageal sphincter. The elongated expandable member can form a non-compliant or semi-compliant shape that is anatomically complementary to the upper esophageal sphincter when expanded. After positioning, the elongated expandable member is expanded within the interior passage of the upper esophageal sphincter such that the elongated expandable member complimentary supports a natural shape of the upper esophageal sphincter.

In some embodiments, expanding the elongated expandable member includes differentially inflating separate inflatable portions of the elongated expandable member.

DETAILED DESCRIPTION OF THE INVENTION

Figure 1A:
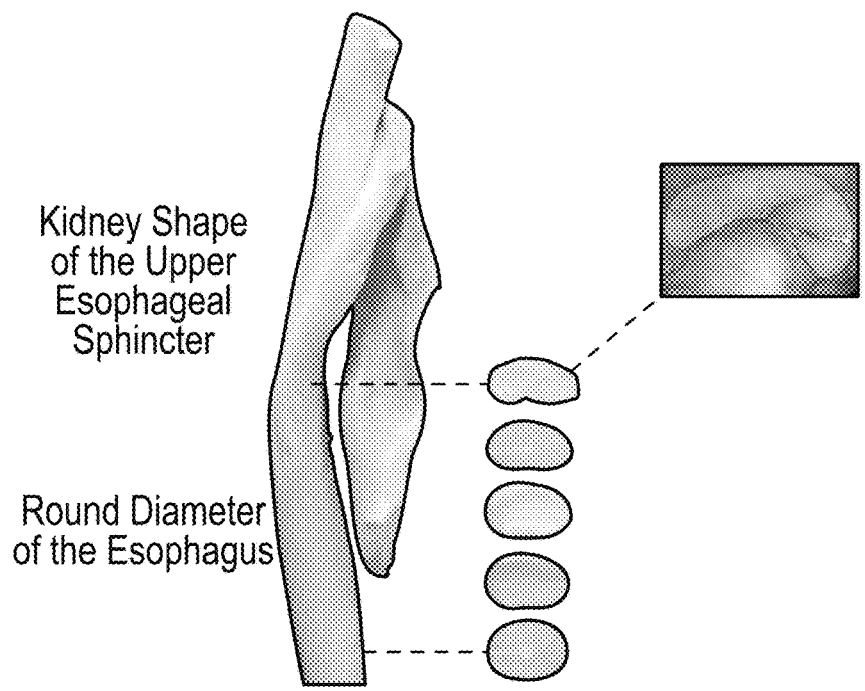
FIG. 1A shows a casting of an upper esophageal sphincter.

Some embodiments of invention include a balloon dilator that approximates the natural (pre-radiated) biological dimensions of the upper esophageal sphincter. As shown in FIG. 1A, a cast of the upper esophageal sphincter in sheep confirmed that the diameter of the body of the esophagus is round and that the UES is kidney bean shaped, that is, having a cross-section having two separate curve-like profiles. Current esophageal dilators are cylindrical and assume a round luminal cross-sectional area.

Impressions of the upper aerodigestive tract were made from 10 cadaveric dorper cross ewes. An incision was made to isolate the distal esophagus and retrograde injections of silicone molding were performed to cast the UES. The silicone was allowed to harden for 30 minutes and then excised from each cadaver. A 5 mm cross-section of the narrowest region of the UES and 2 cm below this region in the cervical esophagus was obtained. The sections were digitally rendered and the pixels were mathematically modeled utilizing a fourth-order polynomial equation.

The narrowest region through the UES approximated a quartic polynomial and the region of the proximal esophagus approximated an ellipse. This suggests that the shape of the UES resembles a kidney bean and the cervical esophagus more approximates a circle.

Figure 1B:
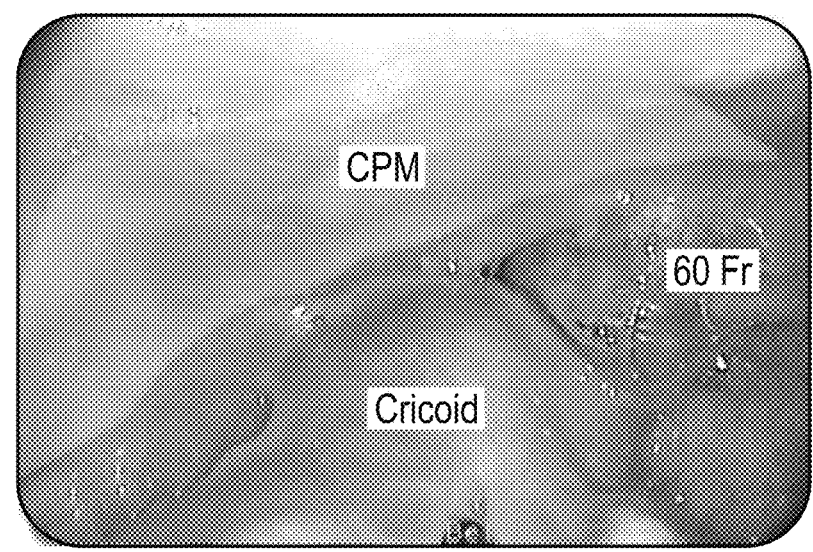
FIG. 1B shows a view of a prior device being used to incompletely dilate an upper esophageal sphincter.
Figure 1C:
FIG. 1C shows a view a device being used to dilate an upper esophageal sphincter, according to an embodiment of the invention.

Thus, it was confirmed that the UES cross sectional area is not round, but rather approximates a kidney bean shape. This work supports the notion that current dilators are not optimal for achieving maximal UES expansion. FIG. 1B shows that the area of the UES is not effectively dilated with a currently available cylindrical dilator with a round circumference. In contrast, FIG. 1C shows that the UES is very effectively dilated when using an expandable member according to an embodiment of the invention.

Figure 2:
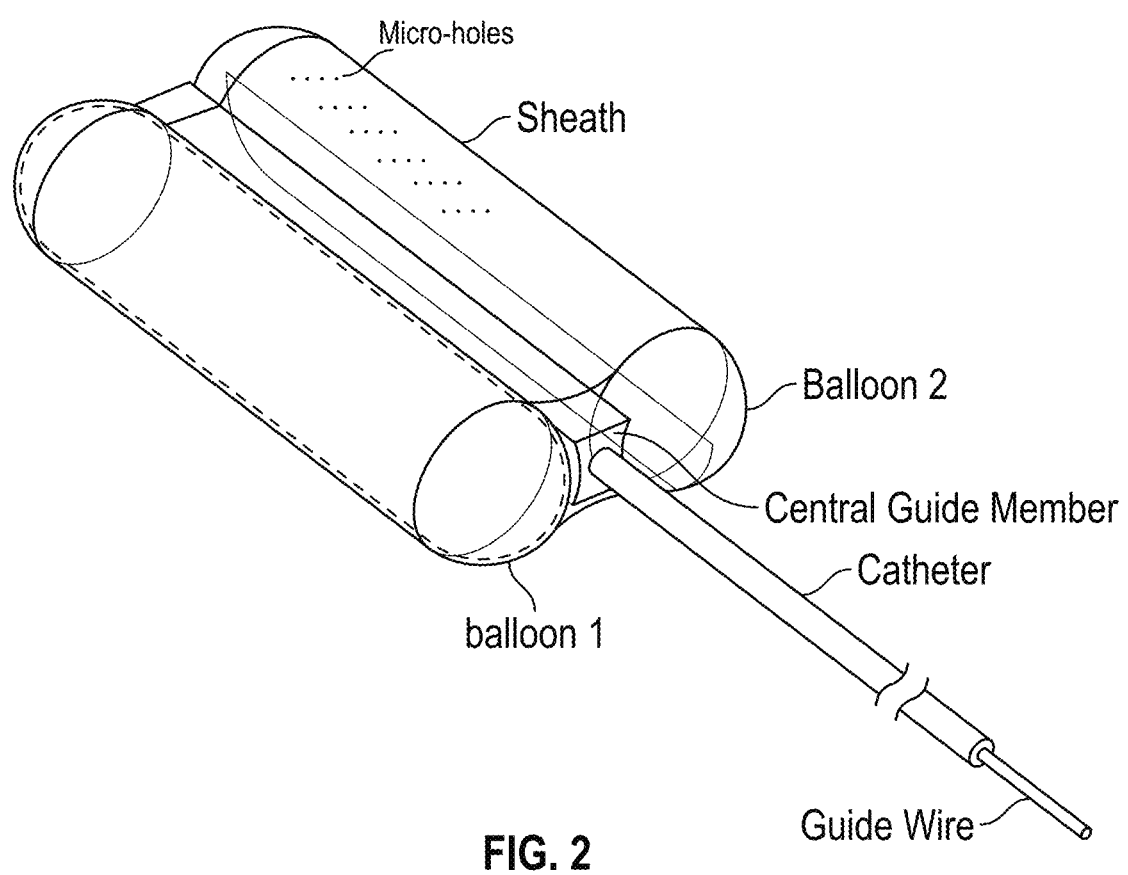
FIG. 2 shows a perspective view of a device for dilating an upper esophageal sphincter, according to an embodiment of the invention.

As shown in FIG. 2, Some embodiments of invention may include an expandable member having a cross-section shaped like a kidney bean, which can be approximated by two cylindrical dilators in apposition. The dilator may possess one or two insertion catheters. There may be advantages to having one or two insertion catheters.

Each balloon may be inflated independently or in unison, and accordingly be in fluid communication with respective catheters to establish inflation. Alternatively, a single catheter with multiple passages can serve to provide pressurization fluid to all balloons. At least one of the catheters may be configured with a passage to enable travel over a guide-wire.

A central guide member can be used to connect a plurality of balloons together, as well as for connection to an elongated catheter. The central guide member can be, for example, an elongated member with at least one passage fluidly coupled between the catheter and at least one balloon for fluid passage therein. The central guide member and/or inflatable member can include radiopaque features to allow for visibility under fluoroscopy.

A kidney shaped balloon dilator can be fabricated through a number of techniques. These techniques may relate to the molding of the balloon, twisting of the balloon, or fabricating a seam in the balloon, or fabricating without balloons together to approximate the appropriate shape of the UES. The expandable member can be constructed from a non-compliant or semi-compliant material that is preconfigured to approximate the natural shape of an upper esophageal sphincter when expanded.

In some embodiments, the expandable member can include a sheath that acts to align and maintain outer expanded dimensions of the expandable member, in order to more closely approximate the natural shape of an upper esophageal sphincter. In such embodiments, the sheath can cover one or more inner balloons.

In some embodiments, the expandable member includes a drug delivery system for delivery of a therapeutic substance, such as a drug. For example, drugs can be coated in dry or gel forms on the outer surface of the expandable member and eluted into the wall of an upper esophageal sphincter over a time period when the expandable member is expanded. Examples of such a therapeutic substance include mitomycin-C and steroids, however, other substances can also be used in lieu of or in addition to. In some embodiments, different therapeutic substances are sequentially delivered via, for example, a plurality of different expandable members, with each carrying a different therapeutic substance.

In some embodiments, the outer wall of the expandable member can be constructed from or additionally include a porous or semi-porous surface material (e.g., fabric, sponge, micro grid, ePTFE) which can effectively serve to carry or scaffold a drug solution. Thus, the expandable member can be, for example, dipped, rolled, and/or soaked in a drug solution prior to insertion into the esophagus in order to be prepared for delivering the drug solution to the upper esophageal sphincter.

In some embodiments, the expandable member can include micro-holes configured to elute liquid drug solution into the wall of an upper esophageal sphincter over during expansion. In such embodiments, one or more inner balloons can expand within a bladder-like and porous drug-carrying balloon. A liquid drug solution is held or delivered into the space between the outer portions of the one or more inner balloons and the drug-carrying balloon. Expansion of the one or more inner balloons causes the liquid drug solution to excrete out of the drug-carrying balloon and thereby deliver the liquid drug solution to the wall of an upper esophageal sphincter.

In use and in some embodiments, to dilate the upper esophageal sphincter, a guide-wire can be first inserted into an esophagus of a patient. This may be performed via fluoroscopy and/or bronchoscopy. However, in some embodiments, a guide-wire is not required. While the guide-wire is maintained in position, the expandable member can be fed over the guide-wire via its hand manipulation of its attached catheter, such that the (yet to be expanded) expandable member is placed within the upper esophageal sphincter. The expandable member can then be expanded for a certain amount of time (e.g., 30 seconds) for one or more periods of time. In some embodiments, a therapeutic substance can be delivered to the upper esophageal sphincter during expansion thereof by the expandable member. When the therapy is compete, the expandable member and guide-wire can be removed.

While the exemplary embodiments have been described in some detail for clarity of understanding and by way of example, a number of modifications, changes, and adaptations may be implemented. Further, any dimensions mentioned are exemplary guidelines for one skilled in the art, and thus do not necessarily represent limitations as to size and/or proportion of embodiments of the invention.

What is claimed is:

1. An apparatus comprising:
    an elongated expandable member shaped to support a natural shape of an upper esophageal sphincter, wherein the elongated expandable member comprises:
        a first elongated balloon,
        a second elongated balloon adjacently coupled to the first elongated balloon, wherein the first elongated balloon and the second elongated balloon extend parallel and in apposition to each other from a distal end of each balloon to a proximal end of each balloon, and
        a central guide member located between the first and second elongated balloons; and
    a catheter coupled to and extending from the central guide member, parallel to the elongated expandable member, wherein the central guide member includes a fluid passage from the catheter to the first elongated balloon and the second elongated balloon.

2. The apparatus of claim 1, further comprising an outer sheath wrapped around the first and second elongated balloons.

3. The apparatus of claim 1, wherein the first and second elongated balloons are configured to be differentially inflated.

4. The apparatus of claim 1, wherein the elongated expandable member comprises one or more micro-holes that are configured to elute a therapeutic substance.

5. A method comprising:
  inserting the apparatus of claim 1 into an interior passageway of the upper esophageal sphincter; and
  expanding the elongated expandable member within the interior passage of the upper esophageal sphincter such that the elongated expandable member complimentary supports the natural shape of the upper esophageal sphincter.

6. The method of claim 5, wherein expanding the elongated expandable member comprises differentially inflating the first elongated balloon and the second elongated balloon of the elongated expandable member.

* * * * *